US010470876B2

(12) United States Patent
Gurovich et al.

(10) Patent No.: US 10,470,876 B2
(45) Date of Patent: Nov. 12, 2019

(54) TRANSCATHETER HEART VALVE FOR REPLACING NATURAL MITRAL VALVE

(71) Applicant: Edwards Lifesciences Corporation, Irvine, CA (US)

(72) Inventors: Nikolay Gurovich, Hadera (IL); Mohammad Jafari, Foothill Ranch, CA (US); Liron Tayeb, Peduel (IL); Ilan Tamir, Hefzi-Bah (IL); Ziv Yohanan, Yesud Hamaala (IL); Noam Nir, Gesher Haziv (IL); David Maimon, Haifa (IL); Boaz Manash, Givat Ada (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/345,857

(22) Filed: Nov. 8, 2016

(65) Prior Publication Data

US 2017/0128199 A1      May 11, 2017

Related U.S. Application Data

(60) Provisional application No. 62/253,475, filed on Nov. 10, 2015.

(51) Int. Cl.
*A61F 2/24*      (2006.01)
(52) U.S. Cl.
CPC .......... *A61F 2/2409* (2013.01); *A61F 2/2418* (2013.01)
(58) Field of Classification Search
USPC ................................................. 623/1.1–1.13
See application file for complete search history.

(56) References Cited

U.S. PATENT DOCUMENTS 3,409,013 A    11/1968   Berry
3,472,230 A    10/1969   Fogarty
(Continued)

FOREIGN PATENT DOCUMENTS

CN    102639179 A    8/2012
CN    104220027 A    12/2014
(Continued)

OTHER PUBLICATIONS

Int'l. Search Report issued for PCT/US2016/061171, completed Feb. 20, 2017.

(Continued)

*Primary Examiner* — Yashita Sharma
(74) *Attorney, Agent, or Firm* — Snell & Wilmer L.L.P.

(57) ABSTRACT

Embodiments of prosthetic valves for implantation within a native mitral valve are provided. A prosthetic valve may comprise a radially compressible main body and a one-way valve portion. The prosthetic valve may further comprise one or more ventricular anchors coupled to the main body and disposed outside of the main body. The ventricular anchors may be configured such that a reduced profile of the prosthetic valve is possible. A space may be provided between an outer surface of the main body and the ventricular anchors for receiving native mitral valve leaflets. The prosthetic valve may include an atrial sealing member adapted for placement above the annulus of the mitral valve. Methods and devices for receiving the native mitral valve leaflets between the ventricular anchors and the main body are described.

10 Claims, 15 Drawing Sheets

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,540,782 B1 | 4/2003 | Snyders |
| 6,569,196 B1 | 5/2003 | Vesely et al. |
| 6,575,959 B1 | 6/2003 | Sarge et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |

(56) References Cited

U.S. PATENT DOCUMENTS

| | | |
|---|---|---|
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |
| 8,029,556 B2 | 10/2011 | Rowe |
| 8,092,520 B2 | 1/2012 | Quadri |
| 8,092,521 B2 | 1/2012 | Figulla et al. |
| 8,118,866 B2 | 2/2012 | Herrmann et al. |
| 8,167,932 B2 | 5/2012 | Bourang |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,416,643 B2 | 4/2013 | Magee |
| 8,449,599 B2 | 5/2013 | Chau et al. |
| 8,460,370 B2 | 6/2013 | Zakay |
| 8,652,203 B2 | 2/2014 | Quadri et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0010877 A1 | 1/2007 | Salahieh et al. |
| 2007/0027534 A1 | 2/2007 | Bergeim et al. |
| 2007/0043435 A1 | 2/2007 | Seguin et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0069852 A1 | 3/2010 | Kelley |
| 2010/0131054 A1 | 5/2010 | Tuval et al. |
| 2010/0137979 A1 | 6/2010 | Tuval et al. |
| 2010/0168839 A1* | 7/2010 | Braido .................. A61F 2/2418 623/1.26 |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0264198 A1 | 10/2011 | Murray, III et al. |
| 2011/0288634 A1 | 11/2011 | Tuval et al. |
| 2011/0313515 A1 | 12/2011 | Quadri et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |
| 2013/0190862 A1 | 7/2013 | Pintor et al. |
| 2013/0197622 A1 | 8/2013 | Mitra et al. |
| 2013/0310928 A1 | 11/2013 | Morriss et al. |
| 2014/0046433 A1 | 2/2014 | Kovalsky |
| 2015/0127100 A1* | 5/2015 | Braido .................. A61F 2/2412 623/2.38 |

FOREIGN PATENT DOCUMENTS

| | | | |
|---|---|---|---|
| DE | 2246526 | A1 | 3/1973 |
| DE | 19532846 | A1 | 3/1997 |
| DE | 19546692 | A1 | 6/1997 |

(56) References Cited

FOREIGN PATENT DOCUMENTS

| | | |
|---|---|---|
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| EP | 1849440 A1 | 10/2007 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 93/001768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/28459 A1 | 4/2001 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 05/034812 | 4/2005 |
| WO | 2005/087140 A1 | 9/2005 |
| WO | 05/102015 | 11/2005 |
| WO | 2006/014233 A2 | 2/2006 |
| WO | 2006/034008 A2 | 3/2006 |
| WO | 06/108090 | 10/2006 |
| WO | 06/111391 | 10/2006 |
| WO | 2006/138173 A2 | 12/2006 |
| WO | 2008/005405 A2 | 1/2008 |
| WO | 2008/035337 A2 | 3/2008 |
| WO | 2008/147964 A1 | 12/2008 |
| WO | 2008/150529 A1 | 12/2008 |
| WO | 09/024859 | 2/2009 |
| WO | 2009091509 A1 | 7/2009 |
| WO | 09/116041 | 9/2009 |
| WO | 2010121076 A2 | 10/2010 |
| WO | 2011081997 A1 | 7/2011 |
| WO | 2012/095455 A2 | 7/2012 |
| WO | 2015125024 A2 | 8/2015 |
| WO | 2015188066 A1 | 12/2015 |

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 3735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729 34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluß des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Intery Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Genève, 1991, pp. 5-47.

(56) References Cited

OTHER PUBLICATIONS

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.
EP Search Report dated Jan. 28, 2016 for EP15181583.
EP Search Report dated Feb. 23, 2016 for EP15197122.

\* cited by examiner

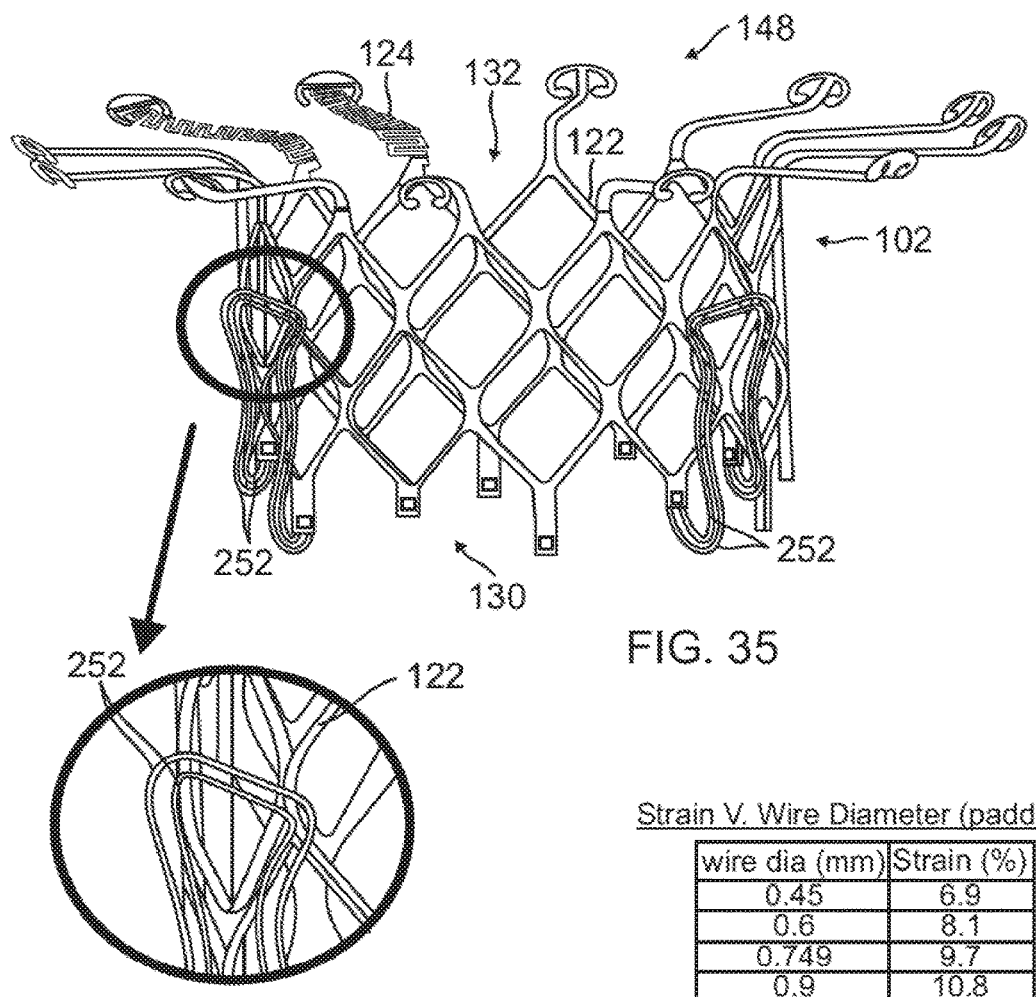
FIG. 35
FIG. 36
Strain V. Wire Diameter (paddle)
| wire dia (mm) | Strain (%) |
|---|---|
| 0.45 | 6.9 |
| 0.6 | 8.1 |
| 0.749 | 9.7 |
| 0.9 | 10.8 |
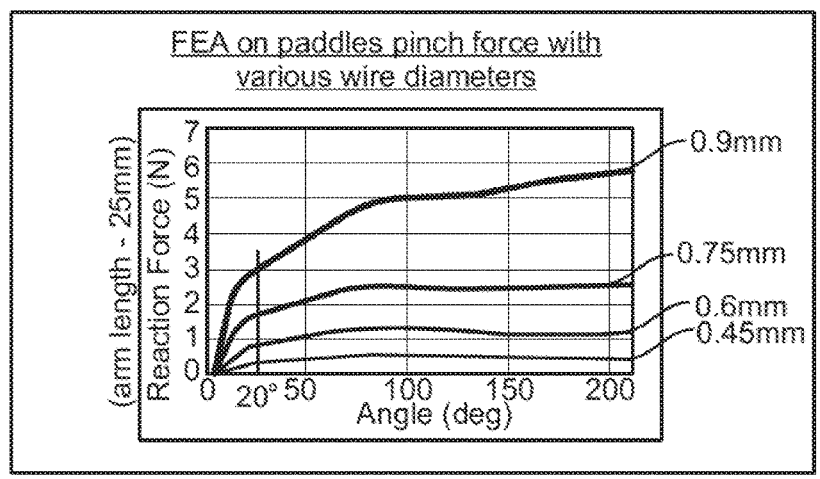
FIG. 37

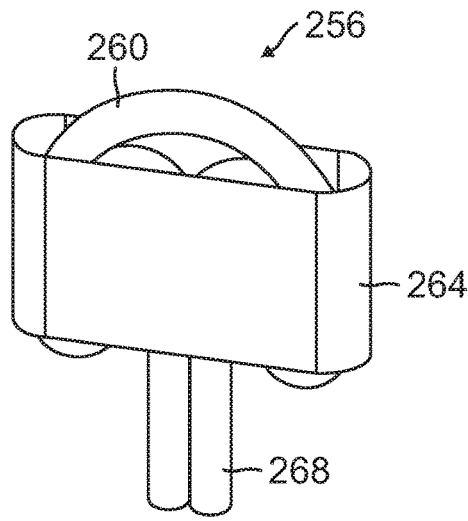
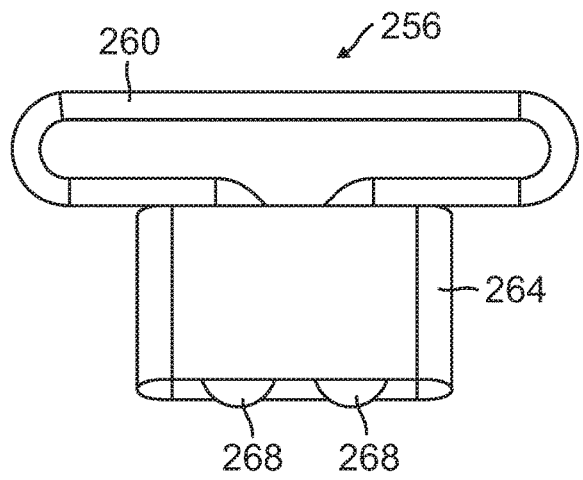
FIG. 38A  FIG. 38B
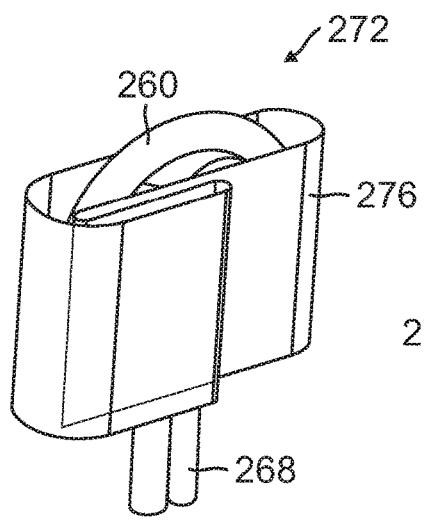
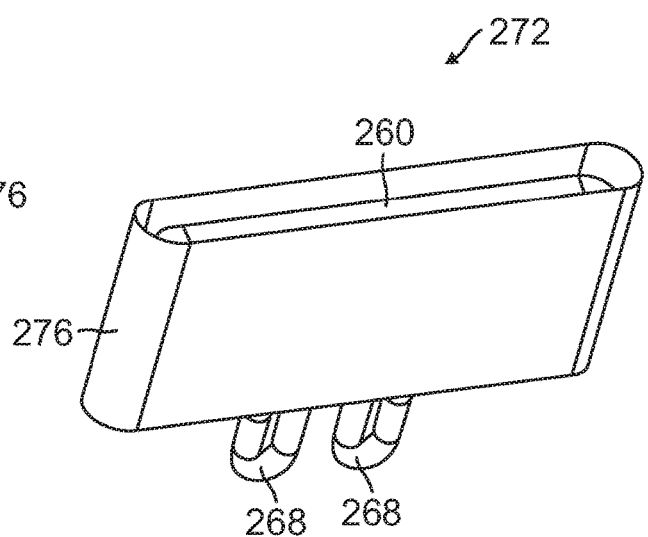
FIG. 39A  FIG. 39B

TRANSCATHETER HEART VALVE FOR REPLACING NATURAL MITRAL VALVE

RELATED APPLICATIONS

This application claims the benefit of U.S. Provisional Application No. 62/253,475, filed Nov. 10, 2015, which is hereby incorporated in its entirety.

FIELD

The field of the present disclosure generally relates to prosthetic devices for repairing and/or replacing native heart valves. More particularly, the field of the invention relates to prosthetic mitral valves having ventricular anchors that contribute to a relatively small crimp profile and are better suited to withstand stresses and strains during delivery into a patient.

BACKGROUND

Prosthetic valves may be used to treat cardiac valvular disorders. Native heart valves, such as aortic, pulmonary, tricuspid, and mitral valves, serve critical functions in assuring a forward flow of an adequate supply of blood through the cardiovascular system. Heart valves can be rendered less effective by congenital malformations, inflammatory processes, infectious conditions, or diseases. Damage to the valves typically results in serious cardiovascular compromise or death. For many years the definitive treatment for heart valve disorders has been surgical repair or replacement of valves by way of open heart surgery. Such surgeries, however, are highly invasive and prone to many complications. As such, elderly and frail patients with defective heart valves often go untreated.

Transvascular techniques have been developed for introducing and implanting a prosthetic heart valve using a flexible catheter in a manner that is much less invasive than open heart surgery. For example, a prosthetic valve may be mounted in a crimped state on an end portion of a flexible catheter and advanced through a blood vessel of a patient until the valve reaches an implantation site of a defective native valve. The prosthetic valve may then be expanded to a functional size at the implantation site such as by inflating a balloon on which the valve is mounted.

Another technique for implanting a prosthetic aortic valve is a transapical approach where a small incision is made in the chest wall of the patient and the catheter is advanced through the apex (i.e., bottom tip) of the heart. Transapical techniques are disclosed in U.S. Patent Application Publication No. 2007/0112422, which is hereby incorporated by reference. As with the transvascular approach, the transapical approach may include a balloon catheter having a steering mechanism for delivering a balloon-expandable prosthetic heart valve through an introducer to a defective native valve. The balloon catheter may include a deflecting segment just proximal to the distal balloon to facilitate positioning of the prosthetic heart valve in a proper orientation within an aortic annulus.

The above techniques and others provide numerous options for high operative risk patients with aortic valve disease to avoid the consequences of open heart surgery and cardiopulmonary bypass. While devices and procedures for aortic valves exist, such catheter-based procedures are not necessarily applicable to the mitral valve due to distinct differences between aortic and mitral valves. For example, the mitral valve has a complex subvalvular apparatus, known as chordae tendineae, which are not present in the aortic valve and can complicate valve delivery and placement.

When the native mitral valve fails to function properly, a prosthetic valve replacement may help restore proper functionality. Compared to the aortic valve, however, which has a relatively round and firm annulus, the mitral valve annulus can be relatively less firm and more unstable. Consequently, it may not be possible to secure a prosthetic valve that is designed for the aortic valve within the native mitral valve annulus by relying solely on friction from the radial force of an outer surface of a prosthetic valve pressed against the native mitral annulus. Accordingly, it may be beneficial to add ventricular anchors to prosthetic mitral valves to help secure the prosthetic valve within the native mitral valve annulus.

However, the addition of ventricular anchors may result in a relatively large crimp profile, including as large as 40 F (i.e., French Gauge). Further, a connection area between the ventricular anchors and the prosthetic valve may experience a relatively high degree of strain during crimping which may give rise to damage to the prosthetic valve during delivery into a patient. A prosthetic mitral valve having ventricular anchors that do not result in an overly large crimp profile or do not increase the size of the crimp profile and comprising a connection area that is better suited to withstand stresses and strains during delivery into the patient.

BRIEF DESCRIPTION OF THE DRAWINGS

The drawings refer to embodiments of the present disclosure in which:

FIG. 35 illustrates an isometric view of an exemplary embodiment of a prosthetic valve comprising multi-wire ventricular anchors;

FIG. 36 is a table showing a relationship between wire thickness and strain induced within the wire due to bending;

FIG. 37 is a graph illustrating a relationship between wire diameter and pinching force of ventricular anchors;

FIG. 38A illustrates an isometric view of an exemplary embodiment of an anchor formed as a T-shaped paddle in a crimped configuration to minimize risk of damage to native leaflets during positioning within the mitral valve region of the heart;

FIG. 38B illustrates an isometric view of the T-shaped paddle of FIG. 38A in an open configuration for pinching the native leaflets;

FIG. 39A illustrates an isometric view of an exemplary embodiment of an anchor formed as a T-shaped paddle in a folded configuration to minimize risk of damage to native leaflets during positioning within the mitral valve region of the heart;

FIG. 39B illustrates an isometric view of the T-shaped paddle of FIG. 39A in an open configuration for pinching the native leaflets;

Figure 1:
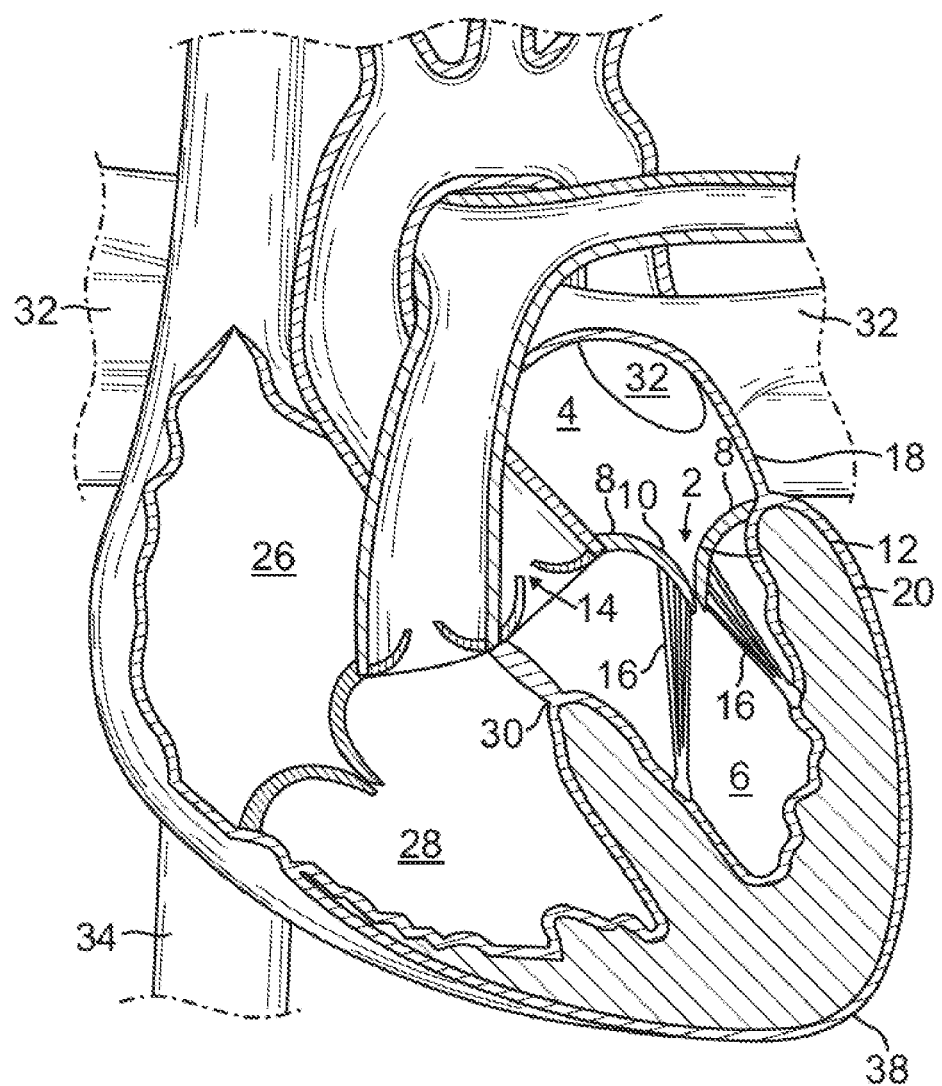
FIG. 1 illustrates a cross-sectional view of a human heart.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first leaflet," may be made. However, the specific numeric reference should not be interpreted as a literal sequential order but rather interpreted that the "first leaflet" is different from a "second leaflet." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

Described herein are embodiments of prosthetic valves and components thereof that are primarily intended to be implanted at the mitral valve region of a human heart. The prosthetic valves may be used to help restore and/or replace the functionality of a defective native mitral valve. However, while the disclosure focuses primarily on mitral valves the concepts, anchors/paddles, etc. are not limited to mitral valves and may be used on prosthetic valves, stents, etc. for use in other regions of the heart or parts of the body.

Figure 2:
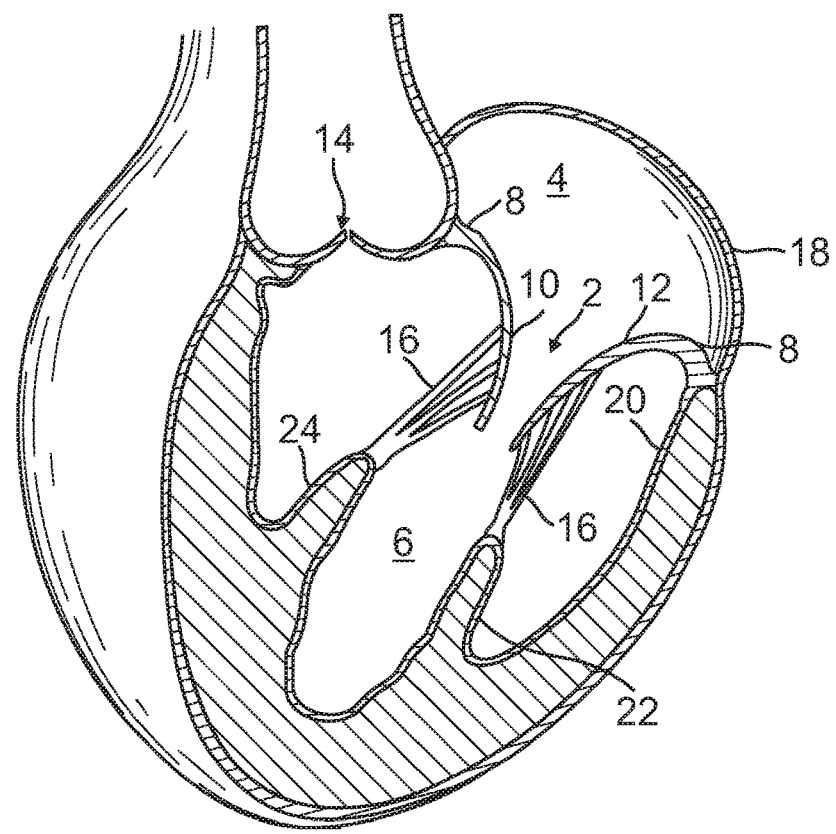
FIG. 2 illustrates another cross-sectional view of the human heart, focusing on a mitral valve region.

FIGS. 1 and 2 illustrate relevant portions of the human heart. A healthy heart has a generally conical shape that tapers to a lower apex 38. The heart is four-chambered and comprises a left atrium 4, a right atrium 26, a left ventricle 6, and a right ventricle 28. The left and right sides of the heart are separated by a wall generally referred to as a septum 30. The left ventricle 6 is bounded by the septum 30 and a wall 20 of the left ventricle. A mitral valve 2 of the human heart connects the left atrium 4 to the left ventricle 6. The mitral valve 2 has a very different anatomy than other native heart valves, such as an aortic valve 14.

Figure 4A:
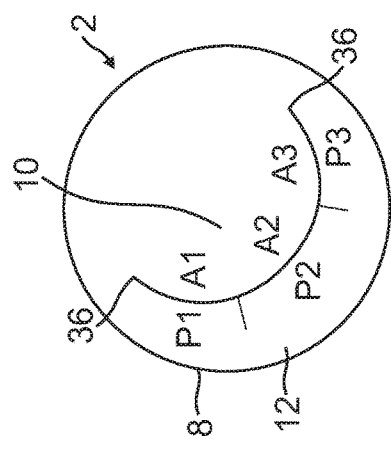
FIG. 4A illustrates a diagram of a native mitral valve, including Carpentier nomenclature.
Figure 4B:
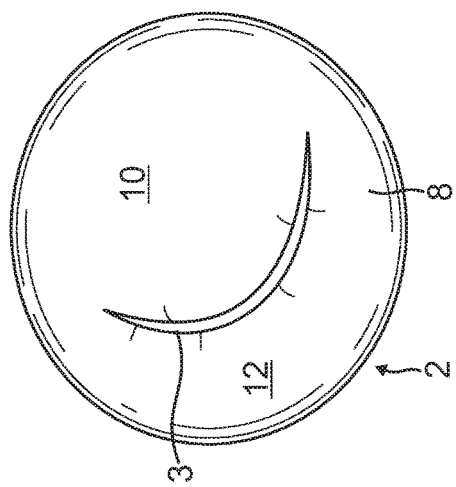
FIG. 4B illustrates a native mitral valve with a gap between the leaflets.

The mitral valve 2 includes an annulus portion 8, which is an annular portion of the native valve tissue surrounding the mitral valve orifice, and a pair of cusps, or leaflets, 10, 12 extending downward from the annulus 8 into the left ventricle 6. The mitral valve annulus 8 can form various shapes, e.g., an oval, "D" shape, saddle shape, bean shape, or some other out-of-round cross-sectional shape having major and minor axes. The anterior leaflet 10 can be larger than the posterior leaflet 12, as shown schematically in FIGS. 4A-4B, forming a generally "C" or curved shaped boundary between the abutting free edges of the leaflets (e.g., when they are closed together). FIG. 4B shows the native mitral valve 2 with a slight gap 3 between the leaflets 10, 12, such as with a defective native mitral valve that fails to completely close (e.g., a mitral valve with an enlarged annulus), which can lead to mitral regurgitation and/or other undesirable conditions.

When operating properly, the anterior leaflet 10 and the posterior leaflet 12 function together as a one-way valve to allow blood to flow only from the left atrium 4 to the left ventricle 6. The left atrium 4 receives oxygenated blood from the pulmonary veins 32. When the muscles of the left atrium 4 contract and the left ventricle 6 dilates, the oxygenated blood that is collected in the left atrium 4 flows into the left ventricle 6. When the muscles of the left atrium 4 relax and the muscles of the left ventricle 6 contract, the increased blood pressure in the left ventricle urges the two leaflets together, thereby closing the one-way mitral valve so that blood cannot flow back to the left atrium and is instead expelled out of the left ventricle through the aortic valve 14.

Figure 3:
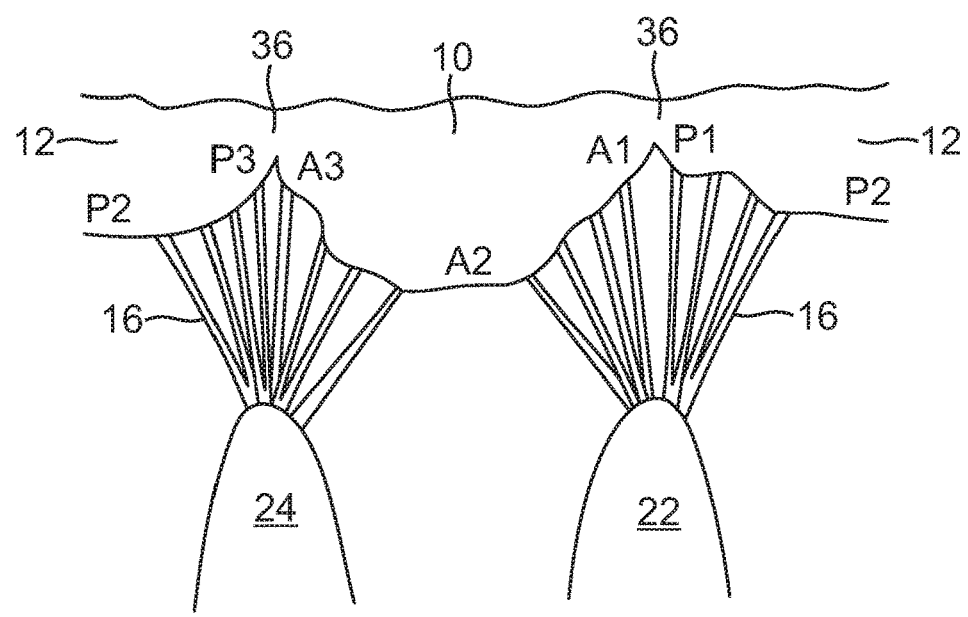
FIG. 3 illustrates a schematic view of a native mitral valve anatomy, showing mitral leaflets attached to papillary muscles by way of chordae tendineae.

To prevent the two leaflets 10, 12 from prolapsing under pressure and folding back through the mitral annulus 8 toward the left atrium 4, a plurality of fibrous cords called chordae tendineae 16 (generally referred to as "chordae" herein) tether the leaflets 10, 12 to papillary muscles in the left ventricle 6. Referring to FIGS. 3 and 4A, chordae 16 are attached to and extend between the postero-medial papillary muscle 22 and the postero-medial margins of both the anterior leaflet 10 and the posterior leaflet 12 (A1 and P1 areas, respectively, as identified by Carpentier nomenclature). Similarly, chordae 16 are attached to and extend between the antero-lateral papillary muscle 24 and the antero-lateral margins of both the anterior leaflet 10 and the posterior leaflet 12 (A3 and P3 areas, respectively, as identified by Carpentier nomenclature). As shown in FIG. 3, the A2 and P2 areas are relatively free of chordae attachment points and provide a region where a prosthetic mitral valve may be anchored. In addition, the organization of the chordae provides an approach path to deliver a prosthetic mitral valve with minimal risk of chordae entanglement.

When the native mitral valve fails to function properly, a prosthetic valve replacement may help restore proper functionality. Compared to the aortic valve, however, which has a relatively round and firm annulus, the mitral valve annulus can be relatively less firm and less stable. Consequently, it may not be possible to secure a prosthetic valve that is designed primarily for the aortic valve within the native mitral valve annulus by relying solely on friction from the radial force of an outer surface of a prosthetic valve pressed against the native mitral annulus. Accordingly, anchors/paddles (e.g., ventricular anchors/paddles) may be added to or used with prosthetic mitral valves, where the anchors operate instead of, or in addition to, radial friction forces, so as to secure the prosthetic valve within the native mitral valve annulus, e.g., as shown in FIG. 5.

In addition to providing an anchoring means for the prosthetic valve, the ventricular anchors can also remodel the left ventricle 6 to help treat an underlying cause of mitral regurgitation—left ventricle enlargement/dilation. The ventricular anchors can pull the native mitral valve leaflets 10, 12 closer together and toward the left atrium and, via the chordae 16, thereby pull the papillary muscles 22, 24 closer together, which can positively remodel the ventricle acutely and prevent the left ventricle from further enlarging. Thus, the ventricular anchors can also be referred to as tensioning members or reshaping members.

Figure 5:
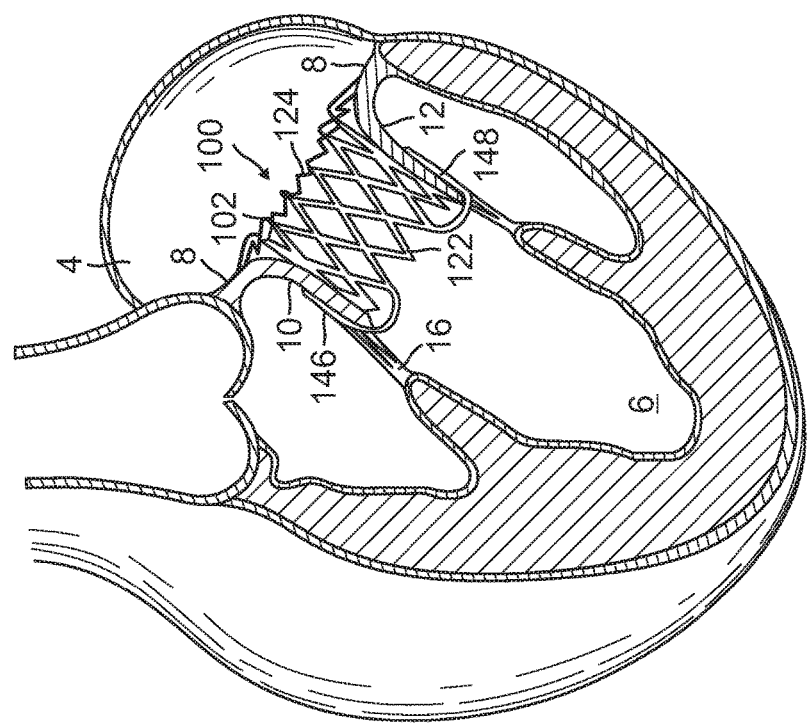
FIG. 5 illustrates a cross-sectional view of the heart, showing a frame of a prosthetic valve implanted in the mitral valve region.
Figure 6:
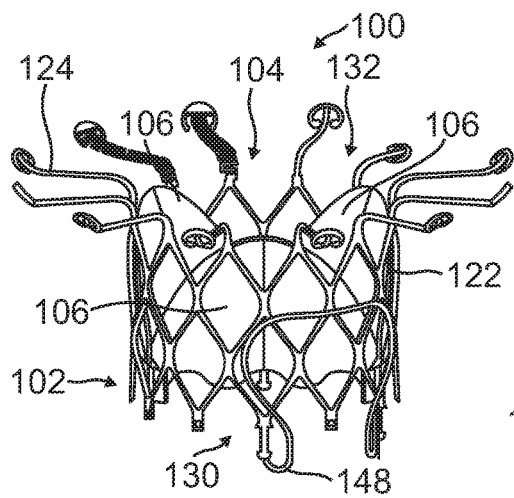
FIG. 6 illustrates an isometric view of an exemplary embodiment of a prosthetic mitral valve comprising ventricular anchors.

FIG. 5 illustrates a cross-sectional view of the human heart showing an exemplary prosthetic valve 100, according to one embodiment, implanted in the native mitral valve region of the heart to replace the functionality of the native mitral valve 2. FIG. 6 illustrates an isometric view of an exemplary embodiment of a prosthetic valve 100 that is substantially similar to the prosthetic valve shown in FIG. 5. The prosthetic valve 100 comprises a frame 102 and a valve structure 104 supported by and/or within the frame. The valve structure 104 may include a plurality of prosthetic leaflets 106 for regulating a flow of blood in one direction through the prosthetic valve 100. As shown in FIGS. 5-6, the frame 102 generally comprises a tubular main body 122, and an anterior ventricular anchor/paddle 146 and a posterior ventricular anchor/paddle 148 extending from a ventricular end 130 of the main body and optionally atrial sealing members/bodies 124 extending radially outward from an atrial end 132 of the main body. When the frame 102 is implanted in the native mitral valve region of the heart, as shown in FIG. 5, the main body 122 is positioned within the native mitral valve annulus 8 with the ventricular end 130 of the main body 122 being a lower outlet end, the atrial end 132 of the main body 122 being an upper inlet end, the ventricular anchors 146, 148 being located in the left ventricle 6, and the atrial sealing members 124 being located in the left atrium 4.

The frame 102 may be made of a wire mesh or another type of stent frame and may be radially collapsible and expandable between a radially expanded state and a radially compressed state so as to enable delivery and implantation at the mitral valve region of the heart, or within another native heart valve. The wire mesh or stent frame may include metal wires or struts arranged in a lattice pattern, such as a saw-tooth or zig-zag pattern shown in FIGS. 5-6 for example, but other patterns may also be used. The frame 102 may comprise a shape-memory material, such as Nitinol for example, to enable self-expansion from the radially compressed state to the expanded state. In some embodiments, the frame 102 may be plastically expandable from a radially compressed state to an expanded state by an expansion device, such as an inflatable balloon (not shown) for example. Such plastically expanding frames may comprise stainless steel, chromium alloys, and/or other suitable materials. The frames could also be partially self-expandable, e.g., the anchors/paddles may be self-expandable, while the main body of the frame may require an expansion device to expand. The various anchors/paddles shown or described herein may be used with a variety of different frames, e.g., any frames shown or described herein or other frames. The various anchors/paddles shown or described herein may also comprise a shape-memory material, such as Nitinol, e.g., to enable the anchor/paddle to move from a compressed or delivery configuration to a different deployed configuration. The various anchors/paddles and/or the exterior surfaces of the various frames described or shown herein could also be textured, coated, or otherwise have a high friction surface to help prevent the prosthetic valve from slipping off the native leaflets and/or dislodging.

Additional details regarding components and assembly of prosthetic valves, as well as techniques for mounting leaflets to the frame, are described, for example, in U.S. Patent Application Publication No. 2009/0276040 A1, U.S. patent application Ser. No. 12/393,010, and U.S. Pat. No. 8,449,599, entitled "Prosthetic Valve for Replacing Mitral Valve," issued on May 28, 2013, the entirety of each of which is incorporated by reference herein.

As best shown in FIG. 5, the anterior and posterior ventricular anchors 146, 148 extend from the main body 122 of the frame 102, such as from the ventricular end 130 of the main body. The ventricular anchors 146, 148 function to retain the frame 102, with or without the valve structure 104, within a native valve region of the heart. In the embodiment shown in FIGS. 5-6, the frame 102 comprises two diametrically opposed ventricular anchors 146, 148 that function to secure the frame 102 to the anterior and posterior mitral leaflets 10, 12, respectively, when the frame 102 is implanted in the mitral valve region. In some embodiments, the frame 102 may comprise one, two, three, four, or more ventricular anchors/paddles, which may be angularly spaced around the main body 122 of the frame, or multiples may be stacked or lined up in the same region (e.g., as discussed with respect to the embodiment in FIG. 35).

When the frame 102 is in an expanded state, as shown in FIGS. 5-6, the geometry of the frame causes the ventricular anchors/paddles 146, 148 to be pressed toward the outer surface of the main body 122. When the frame 102 is radially compressed to a compressed, or crimped, state, the space or gap between the ventricular anchors 146, 148 and the outer surface of the main body 122 may increase, thereby facilitating engagement of the prosthetic valve 100 with the leaflets 10, 12. While the main body 122 and the atrial sealing member 124 are in the crimped state, the frame 102 may be inserted into the mitral valve orifice such that the spaced apart ventricular anchors 146, 148 respectively wrap around the leaflets 10, 12 and extend upward between the leaflets and the walls of the left ventricle 6. With reference to FIG. 5, the anterior ventricular anchor 146 may be located behind the anterior leaflet 10 and the posterior ventricular anchor 148 may be located behind the posterior leaflet 12. With reference to FIGS. 3 and 4A, the two ventricular anchors are desirably located behind the respective leaflets near the middle portions of the leaflets A2, P2 about midway between commissures 36 where the two leaflets meet. These middle portions A2, P2 of the leaflets 10, 12 are desirable ventricular anchor locations because the chordae tendineae 16 attachments to the leaflets are sparser in these locations compared to locations nearer to the commissures 36. The anchors (e.g., ventricular anchors 146, 148) may contribute to a relatively large or larger profile of the prosthetic valve 100 when in the compressed state (i.e., the anchors can add diameter to the valve).

Figure 7:
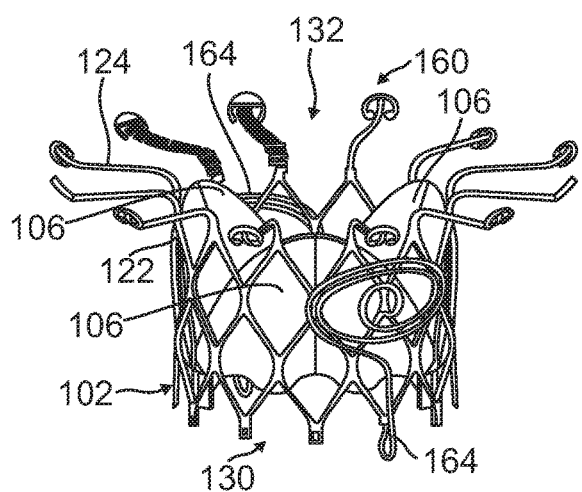
FIG. 7 illustrates an isometric view of an exemplary embodiment of a prosthetic valve comprising anchors formed as wire spiral paddles having a wide oval shape.
Figure 8:
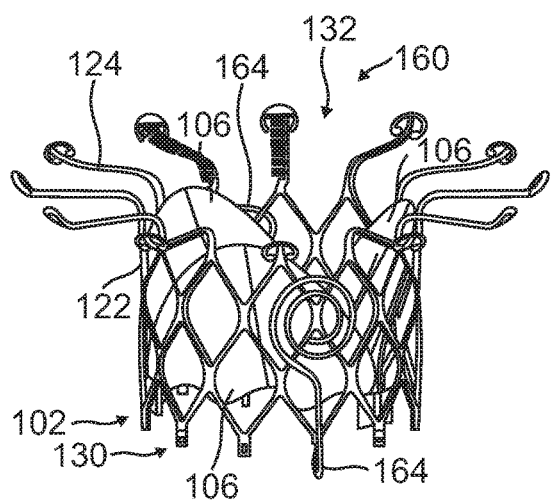
FIG. 8 illustrates an isometric view of an exemplary embodiment of a prosthetic valve comprising anchors formed as wire spiral paddles having a substantially circular shape.

FIGS. 7-8 illustrate an exemplary embodiment of a prosthetic valve 160 comprising ventricular anchors in the form of wire spiral paddles 164 configured to anchor the valve to the native leaflets 10, 12. In the embodiment illustrated in FIG. 7, the wire spiral paddles 164 have a relatively wide oval shape, while the wire spiral paddles 164 illustrated in FIG. 8 comprise a substantially circular shape. The wire spiral paddles 164 generally are comprised of a wire extending from the ventricular end 130 of the main body 122 and coiled into a helix. When the helix presses against the exterior of the main body 122, the helix can flatten into the wire spiral paddles as shown in FIGS. 7-8.

The wire spiral paddles 164 may comprise any number of turns, and may comprise various pitches and/or arrangement of turns so as to control the pressure and force distribution applied to the native leaflets 10, 12. The wire spiral paddles 164 are configured to apply a relatively uniform distribution of force onto the leaflets 10, 12 so as to provide relatively better anchoring of the prosthetic valve 160 within the heart. As will be appreciated, a substantially uniform force distribution operates to reduce pressure concentrations applied to the leaflets 10, 12, and thus reduces a risk of native leaflet abrasions once the prosthetic valve 160 is implanted within the mitral valve region of the heart. Further, the substantially uniform force applied by the anchors (e.g., by wire spiral paddles 164) to the native leaflets 10, 12 generally reduces strain on the anchors, thereby reducing a risk of material fatigue arising with the prosthetic valve 160. The wire spiral anchors/paddles 164 (as well as the other anchors/paddles described herein) may be coated with a soft material or be wrapped or surrounded in a cloth pouch or other padding (e.g., to help protect the native mitral valve leaflets and possibly to provide added friction, for example, with a textured surface or high friction surface). For example, the entire spiral may be wrapped in a cloth pouch (e.g., a wide pouch that surrounds all portions of the spiral in the same area) or a cloth sleeve that runs along the length of the paddle (e.g., the cloth sleeve may be long and narrow and may itself spiral with each turn of the wire).

Figure 9:
FIG. 9 illustrates an isometric view of a prosthetic valve crimped into a forward compressed state.

As mentioned above, the wire spiral paddles 164 significantly reduce the crimp profile of the frame 102. FIG. 9 illustrates an isometric view of the prosthetic valve 160 crimped into a forward compressed state. In the forward compressed state, the wire spiral paddles 164 are shown stretched into a long wavy wire shapes within a delivery system capsule for delivery into the heart. When the wire spiral paddles 164 exit the delivery system capsule, the long wavy wires return to the paddle shape shown in FIGS. 7-8, e.g., the paddles 164 may be of a shape-memory material that will automatically return to the desired shape upon being deployed. In the forward compressed state, the entire paddle may be contained in a cloth sleeve (e.g., a long narrow sleeve; a skirted sleeve). In one embodiment, the cloth sleeve may also move into the spiral shape as the paddle regains the spiral shape when deployed.

Figure 10:
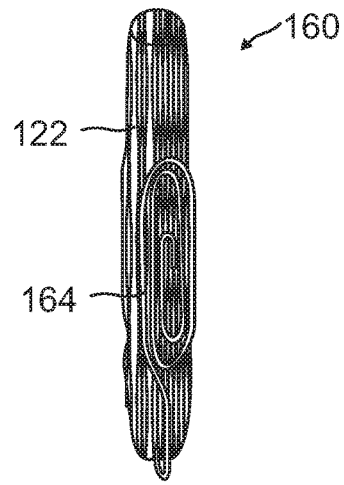
FIG. 10 illustrates an isometric view of a prosthetic valve crimped into a backward compressed state.
Figure 11:
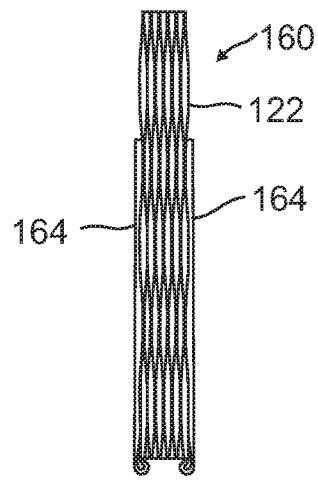
FIG. 11 illustrates a side view of a prosthetic valve crimped into a backward compressed state.

FIGS. 10-11 illustrate respective isometric and side views of the prosthetic valve 160 crimped into a backward compressed state. In the backward compressed state, the anchors or wire spiral paddles 164 are pressed against the exterior surface of the main body 122 within the delivery system capsule, resulting in an elongate oval shape of the paddles.

When the wire spiral paddles 164 exit the delivery system capsule, however, the paddles may return or change to a generally circular or wide oval shape as shown in FIGS. 7-8. Although the backward compressed state gives rise to relatively small strains on the paddles, the forward compressed state advantageously reduces the crimp profile of the prosthetic valve 160 more than the backward compressed state.

As mentioned above, the wire spiral paddles 164 generally are comprised of a wire extending from the ventricular end 130 of the main body 122 and coiled into a helix. When the helix presses against the exterior of the main body 122, the helix can flatten into the wire spiral paddles shown in FIGS. 7-8. In some embodiments, the wire spiral paddles 164 may comprise separate components that are fastened to the frame 102 during assembly of the prosthetic valve 160. In some embodiments, the wire spiral paddles 164 may comprise portions of a single, laser cut frame. As will be appreciated, using a single piece of material to fabricate the frame 102 and the paddles 164 enables the paddles to be advantageously laser cut along with the frame 102. While the frame may be formed by laser cutting the frame into the desired shape, the frame may also be formed in other ways, e.g., other types of cutting, molding, 3D printing, individual assembly and attachment, heat treating, and more.

Figure 12:
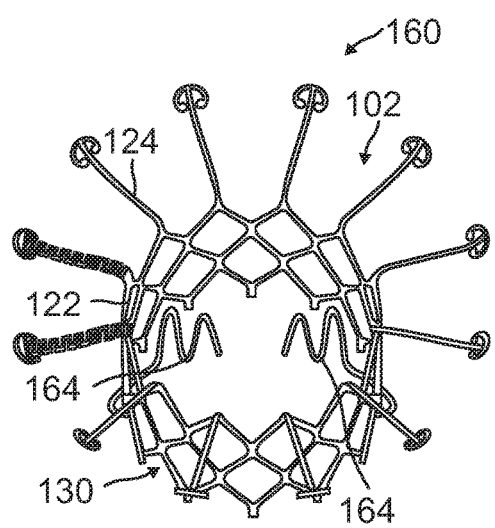
FIG. 12 illustrates anchors formed as wire spiral paddles shaped into inwardly-directed helixes.
Figure 13:
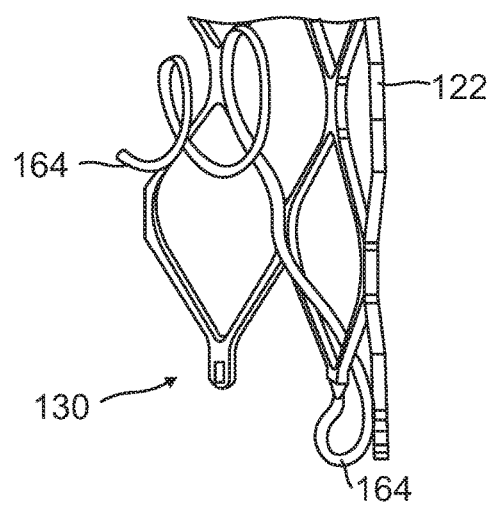
FIG. 13 illustrates a wire spiral paddle shaped into an inwardly-directed helix before being moved into a pressed relationship with a wall of a valve.

After forming (e.g., by laser cutting), the wire spiral paddles 164 may be shaped into a desired shape/form, e.g., as inwardly-directed helixes or 3D spirals as shown in FIGS. 12-13, and then moved to a pressed relationship with the exterior of the main body 122 of the frame 102. Shaping the helixes inside the frame 102 can facilitate biasing the wire spiral paddles 164 toward the center of the frame or against the exterior of the main body 122 (e.g., if pulled out from the interior and set against the exterior of the frame, e.g., to form a paddle similar to that shown in FIG. 8), as well as providing a means for configuring the force distribution that the paddles exert onto the native leaflets 10, 12. Once laser cutting and shaping or other forming of the helixes is completed, the helixes are wrapped into a cloth comprising a biocompatible material suitable for contacting the leaflets 10, 12. In those embodiments of the prosthetic valve 160 that are intended to be delivered by way of the backward compressed state shown in FIGS. 10-11, the helixes may be wrapped into a cloth pouch or other padding. In embodiment of the prosthetic valve 160 that are to be delivered by way of forward compressed state shown in FIG. 9, the helixes may be stretched into long wavy wires, as described above, and then wrapped into a cloth sleeve.

Figure 14:
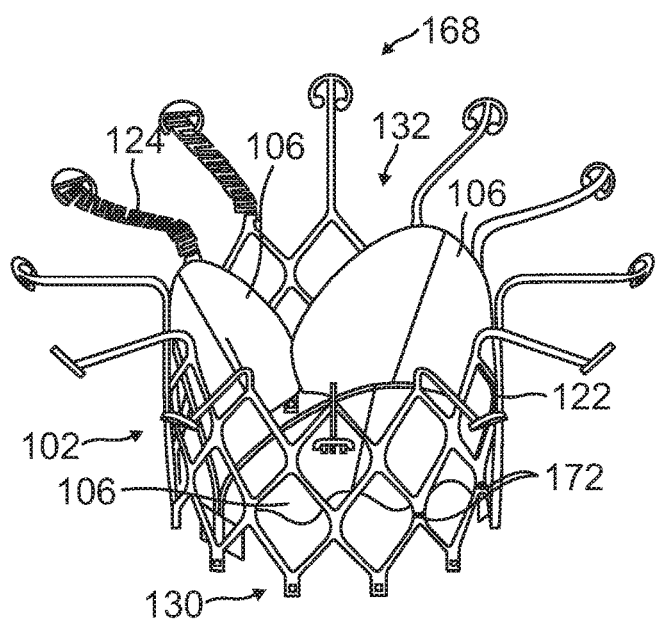
FIG. 14 illustrates an isometric view of an exemplary embodiment of a prosthetic valve adapted for implantation within the native mitral valve region of the human heart.
Figure 15:
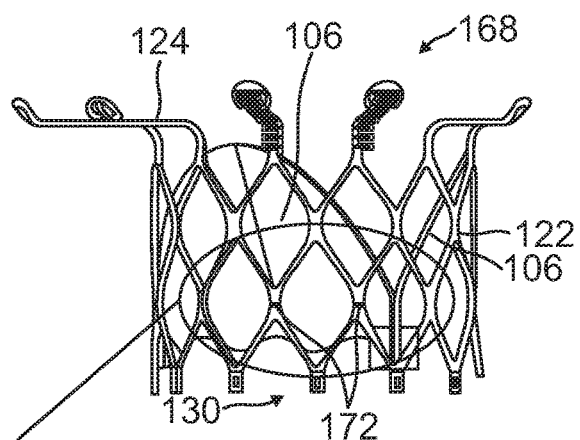
FIG. 15 illustrates a front view of the prosthetic valve of FIG. 14 comprising an interlaced mechanism.
Figure 16:
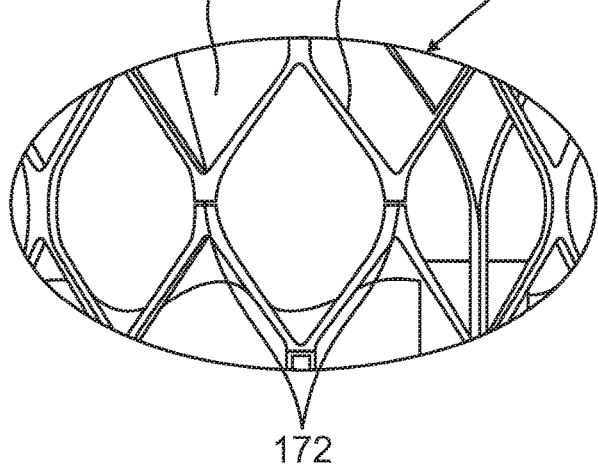
FIG. 16 illustrate a close-up view of the interlaced mechanism of FIGS. 14-15.

FIGS. 14-16 illustrate an exemplary embodiment of a prosthetic valve 168 adapted for implantation within the native mitral valve region of the human heart. The prosthetic valve 168 is substantially similar to the prosthetic valve 160, illustrated in FIGS. 6-8, with the exception that the prosthetic valve 168 comprises an interlaced anchoring mechanism 172 configured to receive the native leaflets 10, 12. As best shown in FIGS. 15-16, the interlaced anchoring mechanism 172 may comprise small cuts along the middle section of the main body 122 that allow portions of the frame 102 below the cuts to act as anchors and engage with the leaflets 10, 12, as described herein. The cut can be along a connection point where multiple struts meet.

Figure 18:
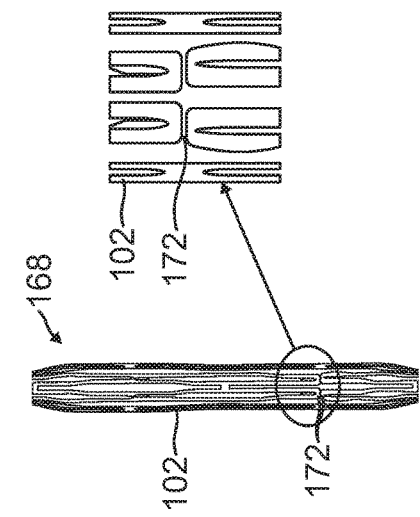
FIG. 18 illustrates a front view of the prosthetic valve of FIG. 14 crimped into a compressed state suitable for residing within a delivery system capsule.
Figure 17:
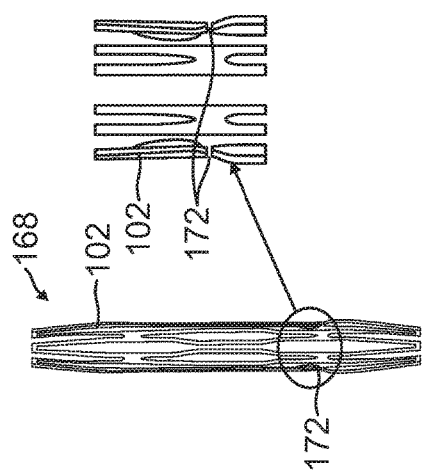
FIG. 17 illustrates a side view of the prosthetic valve of FIG. 14 crimped into a compressed state suitable for residing within a delivery system capsule.

FIGS. 17 and 18 illustrates respective side and front views of the prosthetic valve 168 crimped into a compressed state suitable for residing within a delivery system capsule. As will be appreciated, an entirety of a prosthetic valve 168 has a relatively small profile when residing within the delivery system capsule, and the anchors do not add to the diameter or profile of the valve 168 (e.g., in contrast to an anchor that overlaps the frame and thereby increases the diameter).

Figure 20:
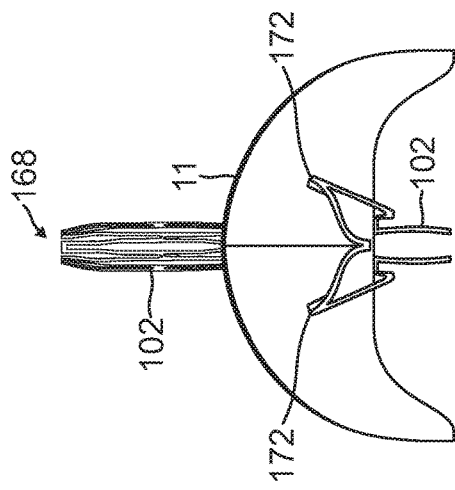
FIG. 20 illustrates a front view of a frame partially expanded with expanded anchor portions being positioned to engage with native leaflets so as to anchor the prosthetic valve of FIG. 14 within the mitral valve region of the heart.
Figure 19:
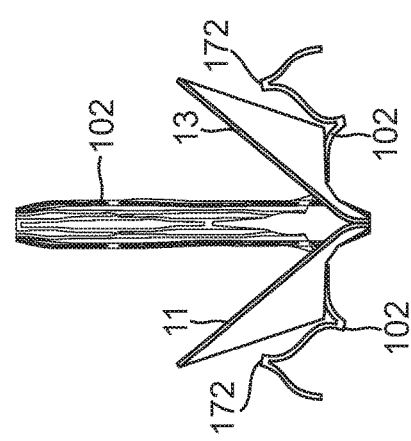
FIG. 19 illustrates a side view of a frame partially expanded with expanded anchor portions being positioned to engage with native leaflets so as to anchor the prosthetic valve of FIG. 14 within the mitral valve region of the heart.
Figure 21:
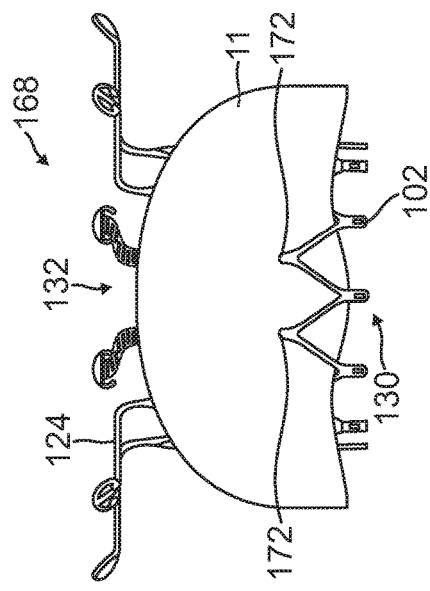
FIG. 21 illustrates a side view of native leaflets engaged with an interlaced anchoring system of a prosthetic valve.
Figure 22:
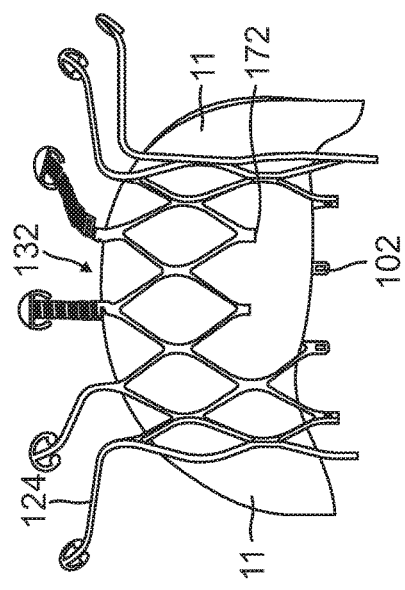
FIG. 22 illustrates a front view of native leaflets engaged with an interlaced anchoring system of a prosthetic valve.
Figure 23:
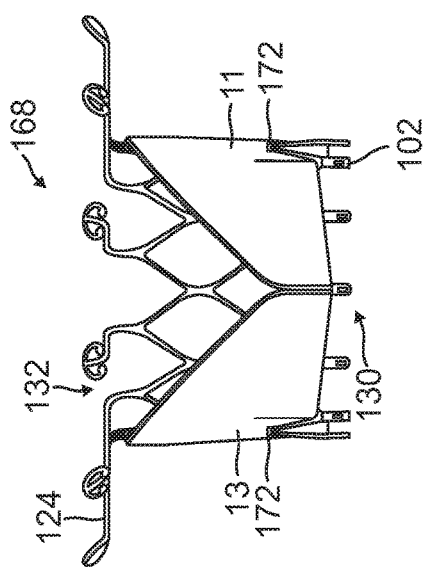
FIG. 23 illustrates an isometric view of native leaflets engaged with an interlaced anchoring system of a prosthetic valve.
Figure 24:
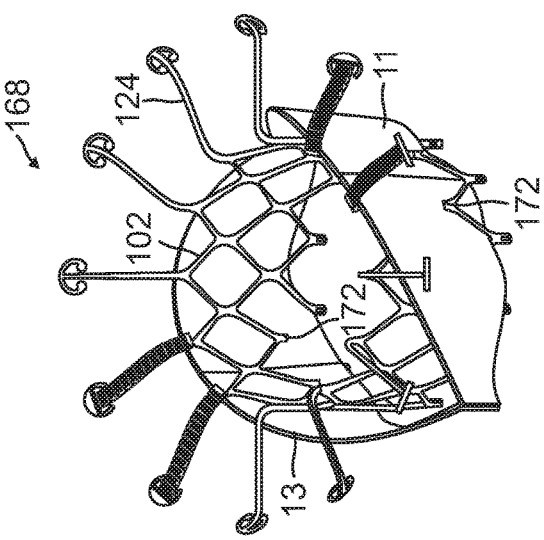
FIG. 24 illustrates a cut-away interior view of native leaflets engaged with an interlaced anchoring system of a prosthetic valve.

When the portion of the prosthetic valve 168 below the interlaced anchoring mechanism 172 exits the delivery system capsule, the cuts allow the exposed portion of the frame to expand to a profile that is larger than the portion of the remaining with the delivery system capsule. This is a partially deployed configuration. As shown in FIGS. 19-20, the expanded portions of the frame 102 may be engaged with the leaflets 11 and 13, which are representative of native leaflets 10 and 12 so as to anchor the prosthetic valve 168 within the mitral valve region of the heart, even when the main body is not fully expanded. Once the entirety of the prosthetic valve 168 exits the delivery system capsule and fully expands, the leaflets 11 and 13 (or native leaflets 10 and 12) are anchored between the main body 122 and the interlaced anchoring system as shown in FIGS. 21-24. Optionally the anchoring mechanism 172 may be covered in a cloth pouch or other padding.

Figure 25:
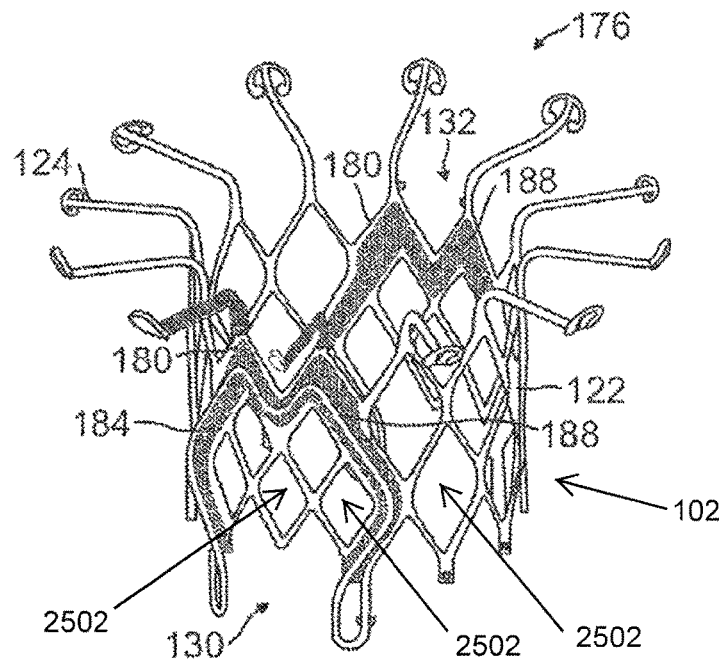
FIG. 25 illustrates an isometric view of an exemplary embodiment of a prosthetic valve configured to exhibit a relatively small profile when crimped into a compressed state, e.g., such that the anchors do not add to the profile.

FIG. 25 illustrates an isometric view of an exemplary embodiment of a prosthetic valve 176 configured to exhibit a relatively small profile when crimped into the compressed state (e.g., the anchors do not add to the profile or diameter because they fit in anchor-receiving regions, shown as a windows in FIG. 25, rather than overlapping the wall of the frame.) The prosthetic valve 176 is substantially similar to the prosthetic valve 100, illustrated in FIG. 6, with the exception that the prosthetic valve 176 comprises anchor-receiving regions or windows 180 that receive anchors/paddles 184 (which include a similar shape to the windows). The windows 180 and the paddles 184 are configured to receive the leaflets 10, 12 there between so as to anchor the prosthetic valve 176 within the mitral valve region of the heart. As will be appreciated, positioning the paddles 184 within the windows 180 significantly reduces the profile of the prosthetic valve 176 when crimped into the compressed state, as compared to a valve that includes anchors or paddles that overlap with the outer wall of the frame, i.e., because the anchors/paddles do not add additional diameter or profile beyond what the frame itself has.

There may be a plurality of openings 2502 defined by the frame 102. When the prosthetic valve 176 is implanted in a native mitral valve, the native leaflets 10, 12 are located between the paddles 184 and the frame 102. In particular, the native leaflets 10, 12 are located between the paddles 184 and two or more of the plurality of openings 2502 of the main body 122. The prosthetic valve 176 may further comprise a skirt 188 disposed within each of the windows 180. The skirts 188 may be configured to keep the paddles 184 circumferentially aligned with the main body 122 of the prosthetic valve when placed into the compressed state. The skirt 188 may be comprised of a biocompatible cloth, Nitinol fiber net, PTFE, ePTFE, or other suitable material having a comparable flexibility and capable of being sutured to cover the windows 180, as shown in FIG. 25. As will be appreciated, the size of the windows 180 and the skirts 188 provides a relatively large contact area between the paddles 184 and the native leaflets 10, 12, and thus local stresses on the leaflets are reduced, and a risk of damage to the leaflets is minimized. Further, in one embodiment the portion of the frame 102 below the windows 180 may be pre-shaped so as to radially protrude outside the circumference of the upper portion of the frame 102. The skirt 188 may be sutured or adhered onto the frame 102 so as to be under continuous tension and thus supply support to the paddles even when the prosthetic valve 176 is in the compressed state. The anchors/ paddles 184 may also be covered with cloth/padding so the native leaflet is compressed between the cloth/padding and skirt 188, which will help prevent damage to the native leaflets. The cloth/padding and/or skirt 188 could also be textured or otherwise have a high friction surface to help hold the native leaflets and prevent dislodging the valve.

As stated above, the prosthetic valve 176 has a relatively small profile when crimped into the compressed state suitable for residing within a delivery system capsule. When the paddles 184 exit the delivery system capsule, however, the windows 180 allow the paddles 184 to expand away from the main body 122, such that the native leaflets 10, 12 may be drawn in between the paddles 184 and the main body. Once the entirety of the prosthetic valve 176 exits the delivery system capsule and fully expands, the native leaflets 10, 12 are then anchored between the main body 122 and the paddles 184.

Figure 26:
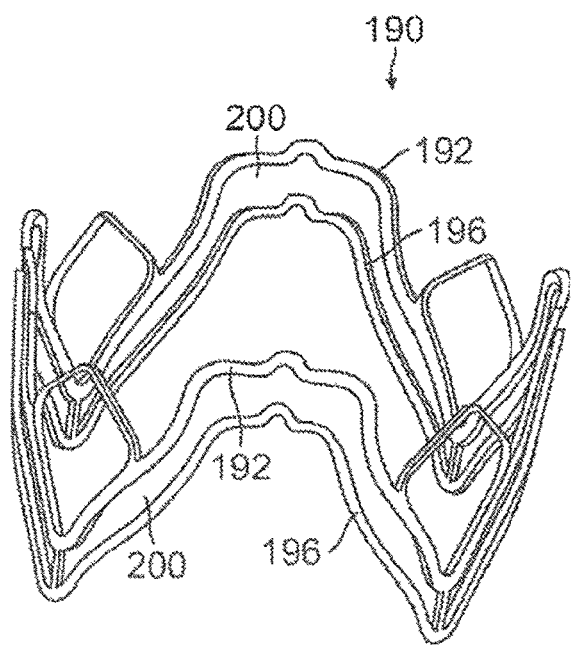
FIG. 26 illustrates an isometric view of an exemplary embodiment of a main body of a prosthetic valve configured to pinch native leaflets in a direction that is parallel to the orientation of the leaflets.
Figure 27:
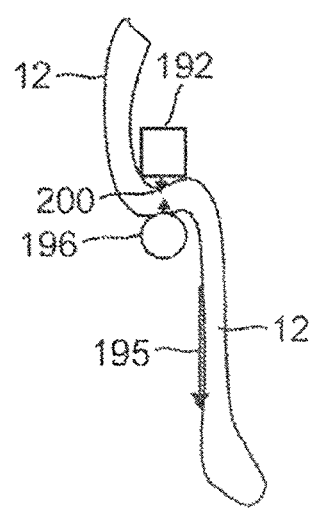
FIG. 27 is a schematic illustrating a native leaflet being pinched in a direction that is parallel to the orientation of the leaflet.

FIG. 26 illustrates an isometric view of an exemplary embodiment of a main body 190 configured to pinch the native leaflets 10, 12 in a direction that is parallel or nearly parallel to the orientation of the leaflets (e.g., general orientation of leaflets indicated by arrow 195 on FIG. 27). The main body 190 comprises frame members 192 that outline anchor-receiving regions that are shaped similar to and can receive anchors/paddles 196 thereunder. The frame members 192 are positioned above corresponding paddles 196, such that windows 200 are disposed there between. In one embodiment, additional frame members similar to frame members 192 could be part of the main body under the frame members 192 and paddles 196, and could form an anchor-receiving region (e.g., a window formed between the additional frame members and the frame members 192 to receiving the anchors/paddles 196). As shown in FIG. 27, the windows 200 are configured to receive the native leaflets 10, 12 such that the paddles 196 and the frame members 192 apply pinching forces (shown in small arrows) in a direction parallel to the leaflets. This can be more secure than pinching forces that are perpendicular to the direction or orientation of the leaflets. In some embodiments, the paddles 196 may be configured to apply pinching forces differently to the anterior leaflet 10 and the posterior leaflet 12. As will be recognized, configuring the paddles 196 to apply pinching forces differently may advantageously accommodate different sizes and shapes that may exist between the leaflets 10, 12.

Figure 28:
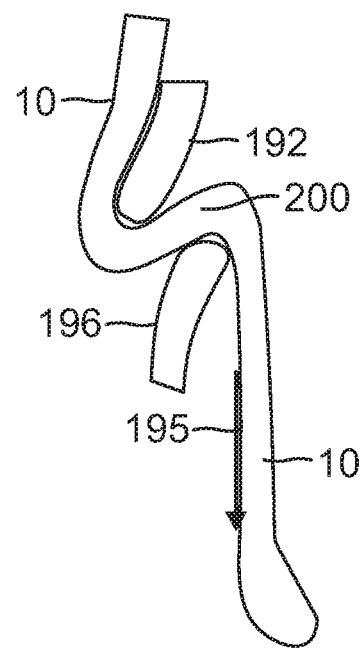
FIG. 28 is a schematic illustrating a native leaflet being gripped by way of a locking mechanism.

In some embodiments, portions of the frame members 192 may be pre-shaped to radially protrude outside the circumference of the main body 190, and the paddles 196 may be pre-shaped to protrude radially inside the main body 190. With the frame members 192 protruding oppositely to the paddles 196, the windows 200 may effectively operate as a locking mechanism capable of gripping the native leaflets 10, 12, as shown in FIG. 28. As will be appreciated, any pulling forces on the leaflets 10, 12, such as forces that may otherwise pull the leaflets loose from the windows 200, will pull the frame members 192 and respective paddles 196 closer together, thereby reducing the sizes of the windows 200 and more tightly gripping the leaflets. Thus, the frame members 192 and paddles 196 provide relatively superior leaflet gripping while eliminating any overlap of the paddles and frame members during crimping of the main body 190.

Figure 29:
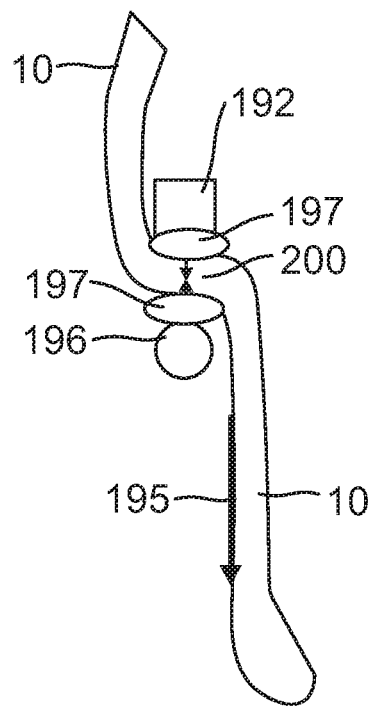
FIG. 29 is a schematic illustrating a soft material layer that operates as a cushion to reduce instances of frictional abrasions or tearing of a native leaflet.

Moreover, the frame members 192 and the paddles 196 may be covered or coated (partially or fully) with a soft material or cloth layer 197 or other padding in order to limit or prevent any damage to the native leaflets 10, 12. As shown in FIG. 29, the soft material or cloth layer 197 may operate as a cushion or padding so as to reduce instances of frictional abrasions or tearing of the leaflet 10, 12. It is envisioned that the soft material layer will add minimally to the profile of the main body 190 in the compresses state.

Figure 30:
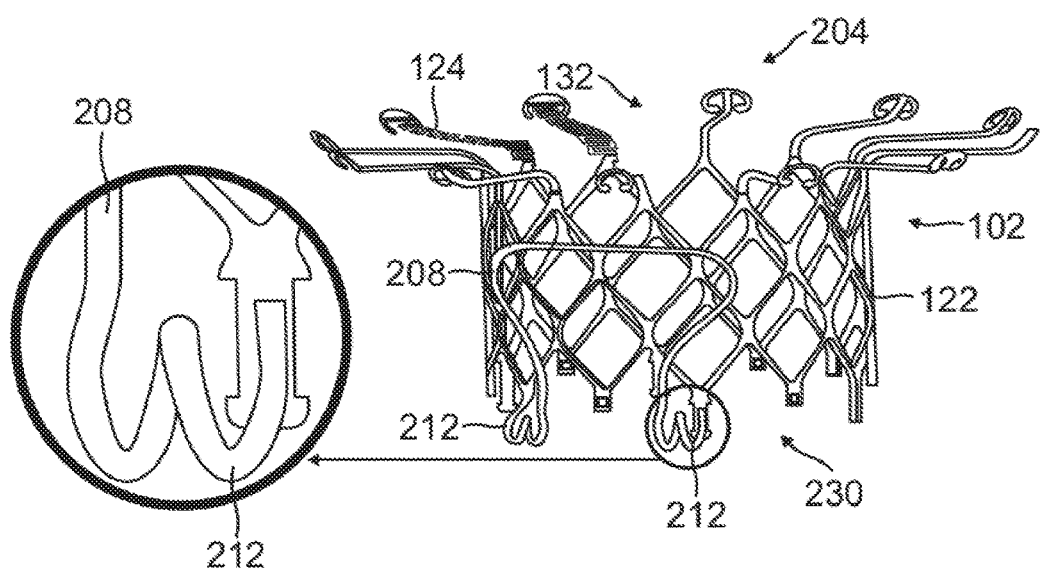
FIG. 30 illustrates an isometric view of an exemplary embodiment of a prosthetic valve configured to be implanted within the mitral valve region of the heart.
Figure 31:
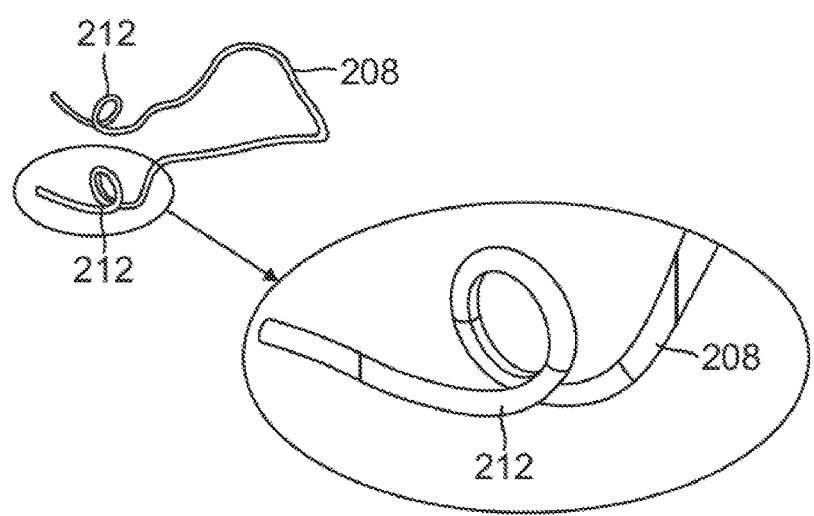
FIG. 31 illustrates an alternate view of the anchor of the prosthetic valve shown in FIG. 30 with the anchor shown in an extended state, e.g., the top of the anchor extends in a direction generally opposite from the bottom ends of the anchor.

FIG. 30 illustrates an isometric view of an exemplary embodiment of a prosthetic valve 204 configured to be implanted within the mitral valve region of the heart. The prosthetic valve 204 is substantially similar to the prosthetic valve 100, illustrated in FIG. 6, with the exception that the prosthetic valve 204 comprises ventricular anchors/paddles 208, that are coupled with the frame 102 by way of connection areas 212 (similar connection areas may also be used with other anchors/paddles described herein). As shown in FIG. 30, each of the connection areas 212 may comprise a spring-shaped wire forming a spring-shaped connection that operates as a hinge configured to distribute strain over a relatively large region of the wire during movement between the paddles 208 and the main body 122. Further, the connection areas 212 provide a relatively small coupling between the paddles 208 and the main body 122, thereby giving rise to a relatively reduced profile when the prosthetic valve 204 is in the compressed state. Further, because the connection areas 212 reduce the strain on the connection between the anchors/paddles and the frame, the paddles may be more easily delivered in a forward position or forward compressed state, e.g., the anchors/paddles may be extended forward so that they do not overlap the frame, but extend from an end of the frame. In this way, the profile may be reduced (i.e., because the anchors/paddles) do not overlap the frame) and there is not too much strain at the connection point because connection areas 212 reduce the strain. FIG. 31 shows an exemplary paddle/anchor 208 extended in a forward position. Although the spring-shaped wire illustrated in FIGS. 30-31 comprises a 360-degree spiral, it should be understood that the spring-shaped wire may comprise spirals having more or less than 360 degrees, without limitation, and without deviating beyond the spirit and scope of the present disclosure.

Figure 32A:
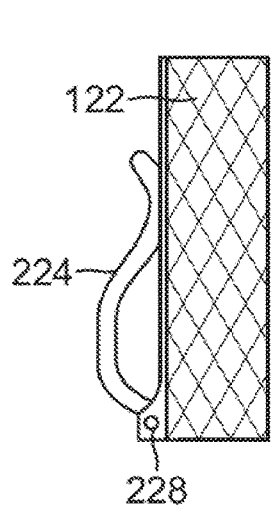
FIG. 32A illustrates a side view of a side portion of an exemplary embodiment of a prosthetic valve 220 configured to be implanted within the mitral valve region of the heart.
Figure 32B:
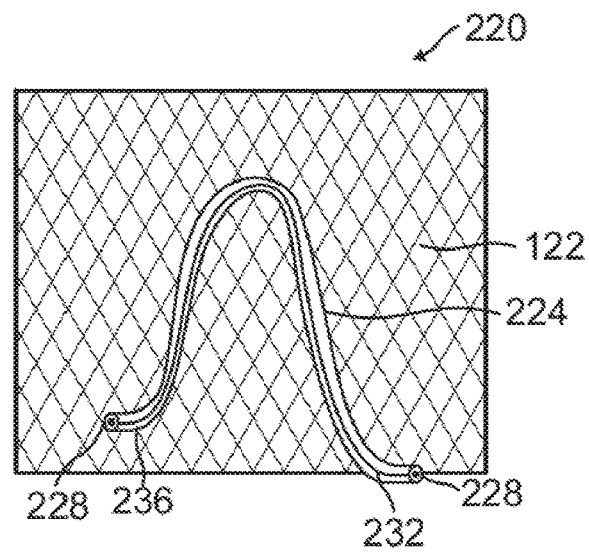
FIG. 32B illustrates a front view of an exemplary embodiment of a prosthetic valve 220 configured to be implanted within the mitral valve region of the heart.

FIG. 32A illustrates a side view of a portion of an exemplary embodiment of a prosthetic valve 220 configured to be implanted within the mitral valve region of the heart. FIG. 32B illustrates a front view of an exemplary embodiment of a prosthetic valve 220 configured to be implanted within the mitral valve region of the heart. A general representation of a frame is shown, but a variety of frame types may be used. The prosthetic valve 220 may be, for example, substantially similar to the prosthetic valves illustrated in FIG. 6 or 30, with the exception that the prosthetic valve 220 comprises anchors or paddles 224 that are coupled with the frame 102 by way of connections or pivoting connections 228. A front view of one paddle 224 is illustrated in FIG. 32B. The paddles 224 may be similar to the paddles 148 in FIG. 6 or paddles 204 illustrated in FIG. 30, with the exception that each of the paddles 224 comprises a first end 232 and a second end 236 that are configured to be slidably received into the pivots 228. The first end 232 generally is longer than the second end 236. Accordingly, the connection/pivot 228 which receives the first end 232 is positioned closer to the ventricular end 130 of the main body 122 than the connection/pivot which receives the second end 236. Similar connections/pivots may be used with other anchors/paddles described herein as well.

Figure 33:
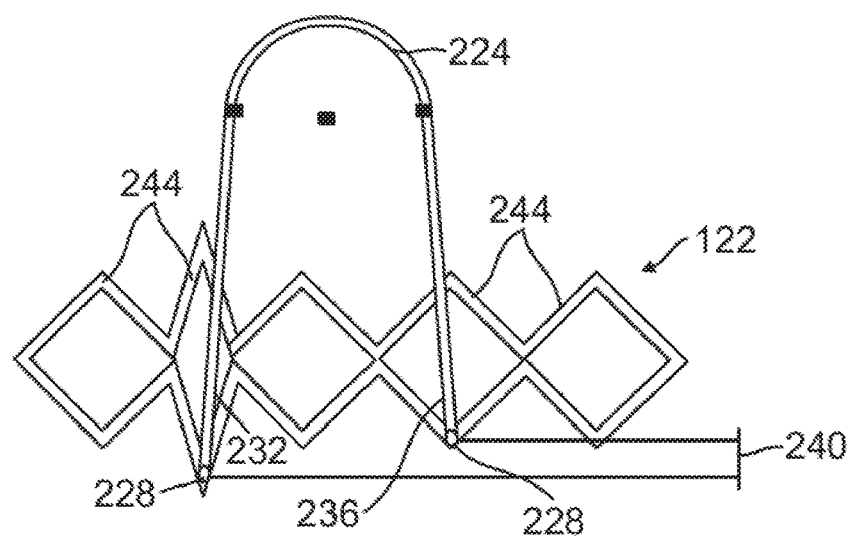
FIG. 33 illustrates a prosthetic valve in an expanded state comprising a height difference between pivots receiving first and second ends of a ventricular anchor.

As best illustrated in FIG. 33, when the prosthetic valve 220 is in an expanded state, a height difference 240 may exist between the pivots 228 receiving the first and second ends 232, 236 of the paddles 224. The height difference 240 restricts movement of the first and second ends 232, 236 within the pivots, and thus causes the paddles 224 to be pressed against the exterior of the main body 122, as shown in FIGS. 32-33. Thus, in the expanded state of the prosthetic valve 220, the paddles 224 may grip or lock on to the native leaflets 10, 12, as discussed herein, due to the height difference 240 of the pivots 228.

Figure 34:
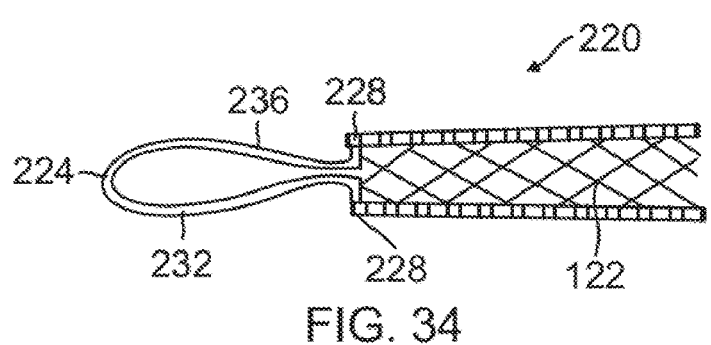
FIG. 34 illustrates the prosthetic valve of FIG. 33 in a compressed state wherein the pivots are aligned and the ventricular anchor is freely moveable and is shown extended.

As further illustrated in FIG. 33, portions of the main body 122 where the pivots 228 receive the first ends 232 of the paddles 224 generally comprise differently sized gaps between struts 244 of the main body 122 than portions elsewhere on the main body. As such, the differently sized gaps between the struts 244 of the main body 122 give rise to the height difference 240 in the expanded state of the prosthetic valve 220. As will be appreciated, however, since all of the struts 244 have the same length, all of the gaps between the struts have essentially the same size when the prosthetic valve 220 is in the compressed state. As best illustrated in FIG. 34, when the prosthetic valve 220 is in the compressed state the pivots 228 may become aligned with one another, thereby allowing the paddles 224 to be freely moveable. In the compressed state, therefore, the paddles 224 may be rotated into a forward position or forward compressed state, such that the profile of the prosthetic valve 220 is relatively small, as illustrated in FIG. 34 (e.g., the anchor/paddle does not add to the profile or diameter because it does not overlap the wall of the frame in the forward position).

FIG. 35 illustrates an isometric view of an exemplary embodiment of a prosthetic valve 248 configured to be implanted within the mitral valve region of the heart. The prosthetic valve 248 may be substantially similar to the prosthetic valve 100, illustrated in FIG. 6, with the exception that the prosthetic valve 248 comprises multiple anchors/paddles 252 or multiple thin wires making up one or more anchors/paddles 252 (or making up other anchors/paddles described herein). The valve 248 may include multiple paddles 252 that are thinner in diameter and/or width than the wires comprising the paddles 146, 148 in FIG. 6. In one embodiment, the valve 248 may include 2-10 (e.g., 2-4 or 2-3) thinner paddles 252 on each of two opposite sides of the valve. The paddles 252 may be stacked, parallel, within the boundaries of another, etc. Other anchors/paddles described herein may also be formed from a combination of multiple thinner wires (e.g., braided together, adjacent each other, or otherwise) forming the anchors/paddles. As shown in FIGS. 36-37, experimentation had demonstrated that thinner paddles (e.g., thin wire paddles) exhibit relatively reduced local strain during bending, while coupling multiple thinner wires together is capable of exerting forces substantially equivalent to, or greater than, single larger diameter wires. Also, multiple thinner wires may prevent concentrated compression on the native leaflet and, thus, prevent damage or tearing. In some embodiments, the multiple wire paddles 252 may comprise a grouping wires each characterized by a unique diameter. The paddles 252 may be stacked, parallel, within the boundaries of another, etc. The multiple paddles/wires may be concentrically aligned or the multiple paddles/wires may be braided together or otherwise connected or associated together in any of various configurations suitable for pinching the native leaflets 10, 12, as described herein. It is further envisioned that the number of wires and the various wire thicknesses may be selected and combined together so as to tailor the forces, local strains, and elastic properties exhibited by the multiple wire paddles 252.

FIGS. 38A and 38B illustrate an exemplary embodiment of T-shaped paddles 256 that are configured to facilitate positioning within the mitral valve region of the heart with a minimal risk of damage to the leaflets 10, 12, misplacement of the prosthesis, or chordae tearing/entanglement. The T-shaped paddle 256 comprises a shape memory wire 260 that is restrained in a crimped configuration by a ribbon 264, as shown in FIG. 38A. As will be appreciated, the crimped configuration of the T-shaped paddles 256 is most suitable for delivery into the heart in a forward compressed state, as discussed herein. Once in the mitral valve region of the heart, the direction of the T-shaped paddles 256 may be reversed and the paddles may be engaged with the native leaflets 10, 12. In the illustrated embodiment, an actuation wire (not shown) may be used to pull the ribbon 264 onto a paddle arm 268 so as to release the shape memory wire 260 into an expanded state, as shown in FIG. 38B. Once in the expanded state, the T-shaped paddles 256 may be used to pinch the native leaflets 10, 12, as discussed herein.

Once the ribbon 264 is placed onto the paddle arm 268, as shown in FIG. 38B, the ribbon generally operates a cushion to reduce the risk of abrasion and tissue damage to anatomical structures within the mitral valve region of the heart. The ribbon 264 may be comprised of a biocompatible cloth, Nitinol fiber net, or other suitable material.

In some embodiments, the ribbon may be comprised of a knitted or folded ribbon that may be opened during expanding of the shape memory wire 260. FIGS. 39A and 39B illustrate an exemplary embodiment of T-shaped paddles 272 comprising a folded ribbon 276. The T-shaped paddle 272 is substantially similar to the T-shaped paddle 256, illustrated in FIGS. 38A-38B, with the exception that the T-shaped paddle 272 utilizes the folded ribbon 276 to maintain the shape memory wire 260 in the compressed state shown in FIG. 39A. In one embodiment, the folded ribbon 276 comprises a knitted cloth that may be unstitched during delivery of the prosthetic valve. In one embodiment, the folded ribbon 276 may be peeled during delivery of the prosthetic valve. Once the folded ribbon 276 is peeled, unstitched, or otherwise unfolded, the ribbon remains disposed on the shape memory wire 260 so as to operate as a cushion to reduce the risk of abrasion and tissue damage to the leaflets 10, 12, as well as anatomical structures within the mitral valve region of the heart.

In the embodiments of 38A-39B and other embodiments in which the anchor has a reduced or narrowed profile during delivery and a larger or broader profile once deployed, this type of configuration may be beneficial in positioning the anchors/paddles in regions including chordae. The reduced or narrowed profile may allow the anchor/paddle to avoid or pass through or around chordae more easily, whereas the larger or broader profile may allow for better anchoring and may help prevent the anchor/paddle from slipping past the chordae and out of position.

As will be appreciated, mitral prostheses with paddles that clamp over the native leaflets 10, 12 may require or may be beneficially provided with frame padding so as to avoid trauma to the leaflets. The padding may be thick to help prevent damage, but the thick padding may a significant amount (e.g., 2 mm to 4 mm or more) to the crimp profile of the prosthesis. As will be recognized, the thickest cross-section generally is around the paddles due to the presence of the frame, frame padding, paddle wire, and paddle padding. One approach to reducing the crimp profile of the prosthesis is to install the padding after delivering the prosthesis.

Figure 40:
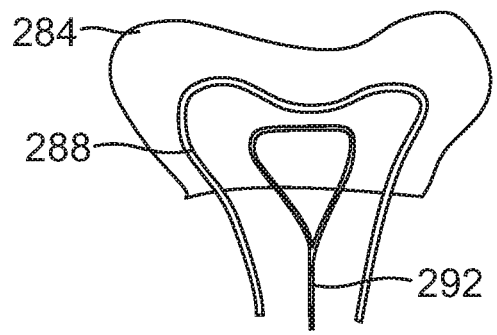
FIG. 40 illustrates an exemplary embodiment of a ventricular anchor/paddle for use on a prosthetic valve that illustrates padding separated from the wire forming the anchor/paddle and shows a pull wire for moving the padding.
Figure 41:
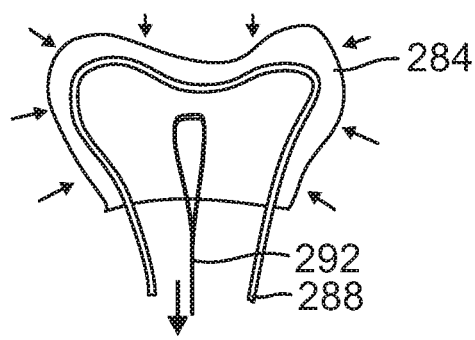
FIG. 41 illustrates the ventricular anchor/paddle of FIG. 40 with the pull wire tensioned to pull the padding into close contact with and surrounding the wire forming the anchor/paddle.

FIGS. 40-41 illustrate an exemplary embodiment of an anchor/paddle 288 and associated padding 284 that may be used with a prosthetic valve (e.g., the valve shown in FIG. 6 or other valves shown or described herein). While anchor/paddle 288 is shown, other anchors/paddles described herein may be used with the padding 284. A padding pocket 284 may be used with the anchor paddle 288 and may be moved into position on a paddle 288 after delivery to the mitral valve region of the heart, e.g., upon deployment but before the paddles 288 are used to pinch the native leaflets 10, 12. In some embodiments, the padding pockets 284 may automatically "jump" onto the paddles 288 when the prosthetic valve 280 is changed from the compressed state to the expanded state, e.g., the padding pocket may be tied to the frame in a way that in the compressed state there is enough slack for the padding pocket to be removed from the anchor/paddle, but when transitioned to the expanded state, the padding pocket may be automatically pulled onto the anchor/paddle as the slack is removed due to the expansion. In some embodiments, such as the embodiments illustrated in FIGS. 40-41, an actuation wire 292, or pull wire, may be incorporated into the prosthetic valve 280. As shown in FIG. 41, the actuation wire 292 facilitates actively pulling the padding pockets 284 onto the paddles 288. In some embodiments, such as the embodiment illustrated in FIG. 40, the padding 284 over the frame 102 may be modular, such that during crimping, the padding 284 may be located separately from the paddles 288, and then the padding 284 may move to the paddles 288 during expanding of the frame 102 so as to provide cushioning between the frame and the native leaflets 10, 12.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Further, features described according to one embodiment above may be combined with features of other embodiments described above, even if not expressly described together. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A prosthetic valve for implantation within a heart, comprising:
    a main body comprising a frame defining a plurality of openings and a first anchor-receiving region, and being configured to be in a radially compressed state during delivery to the heart; and
    a first ventricular anchor being coupled to the frame, having a shape corresponding to the first anchor-receiving region such that the first ventricular anchor is located within the first anchor-receiving region of the frame for achieving a reduced-diameter profile of the frame when the frame is in the radially compressed state, and being configured to receive a native leaflet of a native valve of the heart between the first ventricular anchor and two or more of the plurality of openings to anchor the main body within the native valve.

2. The prosthetic valve of claim 1, wherein the first anchor-receiving region forms a first window in the frame.

3. The prosthetic valve of claim 2, further comprising a skirt disposed within the first window.

4. The prosthetic valve of claim 3, wherein the skirt comprises a biocompatible cloth.

5. The prosthetic valve of claim 1, further comprising a second ventricular anchor having a shape similar to a second anchor-receiving region of the frame and being coupled to the frame such that the second ventricular anchor fits within the second anchor-receiving region of the frame.

6. A prosthetic replacement valve for implantation in a defective native mitral valve, comprising:
    a tubular metallic frame formed with a plurality of openings and a plurality of anchor-receiving regions disposed along a wall of the frame;
    a plurality of prosthetic leaflets mounted within the frame for regulating a flow of blood in one direction through the prosthetic replacement valve; and
    a plurality of ventricular anchors coupled to the frame, each ventricular anchor having a shape corresponding to one of the anchor-receiving regions;
    wherein the ventricular anchors are shaped to be received within the anchor-receiving regions of the frame during delivery of the prosthetic replacement valve to the native mitral valve for reducing a diameter of the prosthetic replacement valve, and
    wherein the ventricular anchors are configured to receive and surround respective native leaflets of the defective native mitral valve between respective ventricular anchors and two or more of the plurality of openings of the tubular metallic frame when the prosthetic replacement valve is implanted in the defective native mitral valve.

7. The prosthetic valve of claim 6, wherein each anchor-receiving region forms a gap in the wall of the frame and wherein each gap corresponds to a shape of a ventricular anchor.

8. The prosthetic valve of claim 7, wherein the ventricular anchors are adapted for capturing native leaflets of the native mitral valve in a space between the ventricular anchors and the frame during implantation and wherein the native leaflets of the native mitral valve are at least partially pulled into the anchor-receiving regions.

9. The prosthetic valve of claim 7, further comprising a fabric skirt disposed within at least one gap in the wall of the frame for assisting with alignment of at least one ventricular anchor with respect to the wall of the frame.

10. The prosthetic valve of claim 9, wherein the skirt comprises a biocompatible cloth.

\* \* \* \* \*